United States Patent
Nakamura

(10) Patent No.: US 9,462,940 B2
(45) Date of Patent: Oct. 11, 2016

(54) OPTOMETRIC APPARATUS

(71) Applicant: NIDEK CO., LTD., Gamagori-shi, Aichi (JP)

(72) Inventor: Kenji Nakamura, Toyohashi (JP)

(73) Assignee: NIDEK CO., LTD., Gamagori-shi (JP)

( * ) Notice: Subject to any disclaimer, the term of this patent is extended or adjusted under 35 U.S.C. 154(b) by 0 days.

(21) Appl. No.: 14/170,013

(22) Filed: Jan. 31, 2014

(65) Prior Publication Data

US 2014/0211164 A1 Jul. 31, 2014

(30) Foreign Application Priority Data

Jan. 31, 2013 (JP) ................................ 2013-016315

(51) Int. Cl.
*A61B 3/032* (2006.01)
*A61B 3/103* (2006.01)
*A61B 3/00* (2006.01)

(52) U.S. Cl.
CPC ............. *A61B 3/032* (2013.01); *A61B 3/0008* (2013.01); *A61B 3/103* (2013.01)

(58) Field of Classification Search
CPC ...... A61B 3/06; A61B 3/063; A61B 3/0008; A61B 3/032; A61B 3/1015
USPC ....................................................... 351/221
See application file for complete search history.

(56) References Cited

U.S. PATENT DOCUMENTS

| | | | | |
|---|---|---|---|---|
| 4,155,632 A | * | 5/1979 | Wolbarsht | 351/243 |
| 4,859,051 A | * | 8/1989 | Fukuma et al. | 351/211 |
| 5,844,660 A | * | 12/1998 | Uchida et al. | 351/211 |
| 5,844,661 A | * | 12/1998 | Uchida et al. | 351/211 |
| 2012/0162606 A1 | * | 6/2012 | Nakamura et al. | 351/221 |

FOREIGN PATENT DOCUMENTS

JP    A-2005-296541    10/2005

* cited by examiner

*Primary Examiner* — Jordan Schwartz
*Assistant Examiner* — George G King
(74) *Attorney, Agent, or Firm* — Oliff PLC

(57) ABSTRACT

An optometric apparatus includes an optotype presenting optical system for presenting part of a plurality of optotypes corresponding to visual acuity to be measured to an examinee's eye and a visible light source for irradiating illumination light to the optotypes presented to the eye through the optotype presenting optical system. A controller is configured to execute processing of changing a light amount of the illumination light to be irradiated to the optotypes from the visible light source between a predetermined first light amount and a second light amount lower than the first light amount and processing of switching the optotypes to be presented to the eye at the time of changing the light amount of the illumination light from the first light amount to the second light amount.

9 Claims, 3 Drawing Sheets

OPTOMETRIC APPARATUS

CROSS-REFERENCE TO RELATED APPLICATIONS

This application is based upon and claims the benefit of priority from the prior Japanese Patent Application No. 2013-016315 filed on Jan. 31, 2013, the entire contents of which are incorporated herein by reference.

BACKGROUND

This disclosure relates to an optometric apparatus for performing visual acuity measurement (optometry) by presenting optotypes to an eye of an examinee.

Conventionally, there is known an optometric apparatus for measuring the visual acuity of an examinee's eye by use of a plurality of optotypes. For instance, JP-A-2005-296541 discloses an optometric apparatus including an auto-refractometer for objectively measuring eye refractive power, provided with a visual acuity chart (corresponding to an optotype plate of an embodiment which will be explained later) having a plurality of optotypes to measure a visual acuity value and optical systems for presenting the optotypes of the visual acuity chart to the examinee's eye.

SUMMARY

Meanwhile, there is a demand for multiple measurements using a single apparatus, such as normal visual acuity measurement, low-contrast visual acuity measurement, visual acuity measurement in a glare lighting state, and others. On the other hand, an optometric apparatus is preferred to be compact in configuration to reduce an installation space of the apparatus.

This disclosure is directed to provide an optometric apparatus having a compact configuration and being capable of appropriately performing various types of visual acuity measurements.

To achieve the above purpose, an optometric apparatus provided as a first aspect is an optometric apparatus includes: an optotype presenting part including a plurality of optotypes corresponding to visual acuity to be measured and being configured to present part of the plurality of optotypes to an examinee's eye; and a controller configured to switch a measurement mode of a visual acuity test between a first measurement mode and a second measurement mode in which a visual acuity value of the examinee's eye is apt to become lower than in the first measurement mode and configured to switch the optotypes at a time of switching from the first measurement mode to the second measurement mode.

Furthermore, an optometric apparatus provided as a second aspect is an optometric apparatus including: an optotype plate having a plurality of optotypes corresponding to visual acuity to be measured; an optotype presenting part configured to selectively present part of the plurality of optotypes of the optotype plate to an examinee's eye; an illumination light source to irradiate illumination light to the optotype plate; and a controller configured to change output of the illumination light source or drive a filter for restricting light traveling from the illumination light source toward the optotype plate to change a light amount of the illumination light to be irradiated to the optotype plate from a first light amount to a second light amount lower than the first light amount and configured to switch the optotypes to be presented to the examinee's eye by the optotype presenting part from among the optotypes of the optotype plate at a time of switching the first light amount to the second light amount.

Still further, an optometric apparatus provided as a third aspect is an optometric apparatus including: an optotype plate including a plurality of optotypes corresponding to visual acuity to be measured; an optotype presenting part configured to selectively present part of the plurality of optotypes of the optotype plate to an examinee's eye; a glare light source configured to emit glare light to the examinee's eye; and a controller configured to switch the glare light source from an unlighted state to a lighted state and switch the optotypes to be presented to the examinee's eye by the optotype presenting part from among the optotypes of the optotype plate at a time of switching the unlighted state to the lighted state.

DETAILED DESCRIPTION OF THE EXEMPLARY EMBODIMENTS

Figure 1:
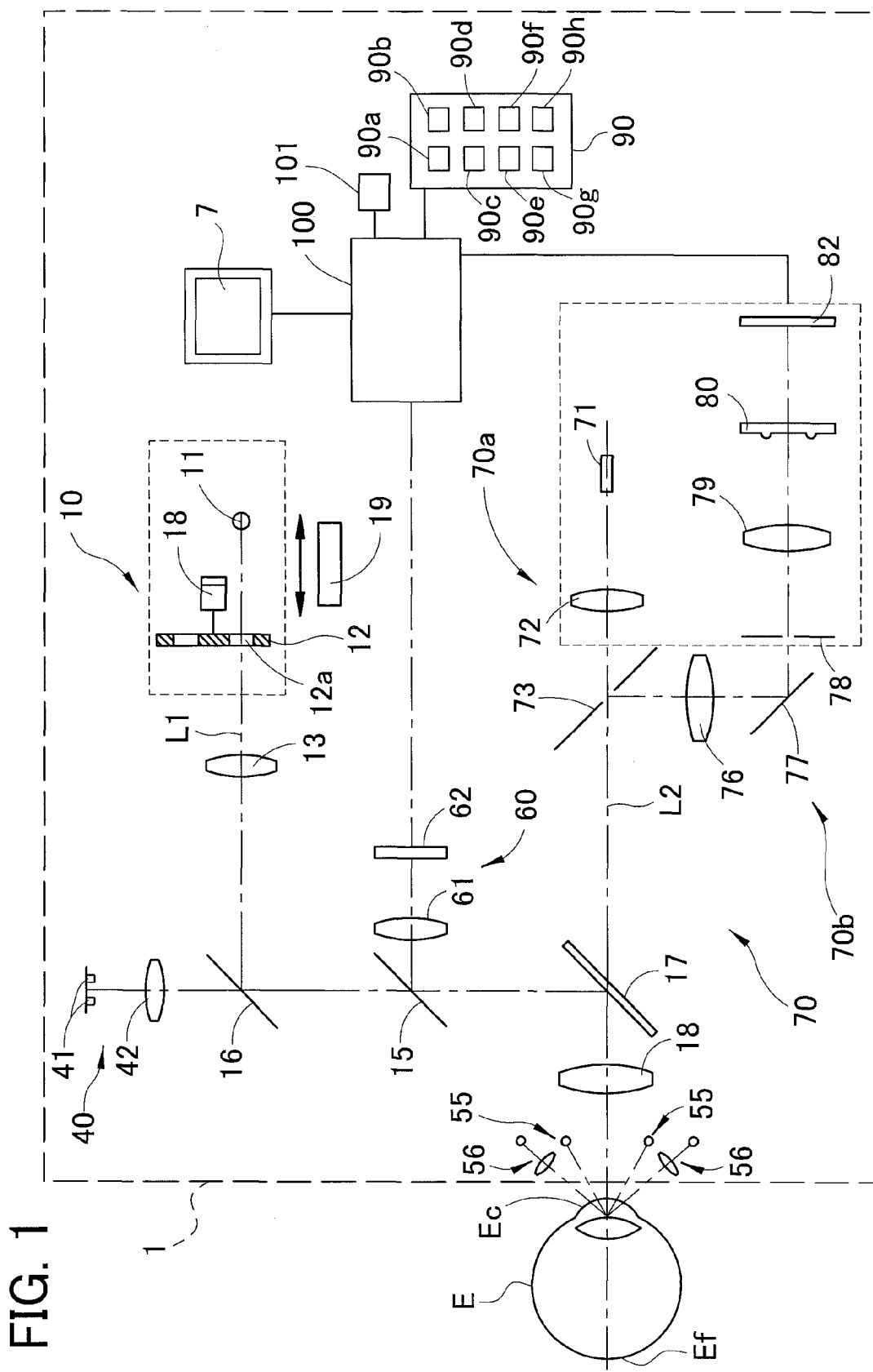
FIG. 1 is a schematic configuration view of optical systems and a control system of an optometric apparatus in an embodiment.

One typical embodiment of this disclosure will be explained below referring to accompanying drawings. FIG. 1 is a schematic configuration view of optical systems and a control system of an optometric apparatus 1 in this embodiment. The optometric apparatus 1 is an optometric apparatus to perform normal visual acuity measurement (so called visual acuity measurement at high contrast), visual acuity measurement at low contrast, and visual acuity measurement in a glare lighting state. In the present embodiment, the normal visual acuity measurement represents the visual acuity measurement to be performed under the condition pursuant to usage conditions of a standard visual acuity test apparatus provided in the Japanese Industrial Standards (JIS). The low-contrast visual acuity is measured by use of optotypes presented at a low contrast ratio between an optotype and a background thereof (optotypes at low contrast) as compared with optotypes for the normal visual acuity measurement (optotypes at high contrast). In the present embodiment, the optometric apparatus 1 will be explained as also functioning to perform objective refractive power measurement. The optical systems and the control system of the optometric apparatus 1 are contained in a casing not shown. This casing may be moved three-dimensionally with respect to an examinee's eye E by a known alignment moving mechanism or may be configured as a handheld device.

The optical systems of the optometric apparatus 1 will be explained first. The optometric apparatus 1 includes, as the main optical systems, an optotype presenting optical system 10, a glare test optical system 40, a ring index projecting optical system 55, and a working distance index projecting optical system 56, an observation optical system (an imaging optical system) 60, and a measurement optical system 70.

The optotype presenting optical system 10 is an optical system for presenting an optotype or optotypes to the examinee's eye E. In the present embodiment, this optotype presenting optical system 10 includes a visible light source 11, an optotype plate 12, a light projecting lens 13, a half mirror 16, a dichroic mirror 17, and an objective lens 18. The optotype plate 12 in the present embodiment is a disk plate having a plurality of optotypes 12a drawn in black on a white body. The optotypes 12a are arranged in a circumferential direction of the optotype plate 12. The optotype plate 12 is connected to a motor 18. When the optotype plate 12 is rotated by the motor 18, the optotypes 12a to be presented to the eye E are changed to another. It is to be noted that the optotype plate 12 also may have a different configuration from the disc plate. For example, it may be an optotype plate formed of a plate material on which a plurality of optotypes are arranged in one direction. In this case, for example, instead of the motor 18, a drive mechanism may be provided to slide the optotype plate with respect to an optical path L1 so that the optotypes face the optical path L1.

In the present embodiment, the optotypes 12a include at least an optotype for visual acuity test (e.g., Landolt ring) to be used in subjective measurement (in visual acuity measurement) and a fixation target to apply a fogging to the examinee's eye E in objective measurement. The optotypes for visual acuity test are prepared in such a manner that optotypes are set in groups of five to be simultaneously presented to the eye E for each visual acuity value (in the present embodiment, the groups are prepared one for each visual acuity value; 0.1, 0.3, 0.5, . . . , 1.5). In the present embodiment, the color density of the optotypes for visual acuity test is uniform between the optotypes 12a.

The above explanation exemplifies that the optotypes for visual acuity test provided in the optotype plate 12 are prepared in groups of five for each visual acuity value in the present embodiment, but the invention is not necessarily limited thereto. The optotypes have only to be prepared one or more per visual acuity value. The visual acuity test optotypes in the optotype plate 12 in the present embodiment are not limited to Landolt rings. For example, the visual acuity test optotypes may be letters, numerals, symbols, figures, and others.

The visible light source 11 is a light source for emitting illumination light to the optotype plate 12 and is used as a fixation light source to make the eye E fixate the optotype plate 12. When the optotypes 12a are illuminated by the visible light source 11, an optotype light beam travels through optical components from the light projecting lens 13 to the dichroic mirror 17 toward the eye E. Accordingly, the optotypes 12a on the optical axis L1 are presented to the eye E. The optotype plate 12 is rotated by the motor 18, thereby selectively placing the optotypes 12a onto the optical axis L1 of the optotype presenting optical system 10. In this manner, the optotypes 12a presented to the eye E are changed to another. This switching of the optotypes 12a to be presented to the eye E can be made not only by driving the optotype plate 12 but also by another technique. For instance, instead of the optotype plate 12, it may be arranged such that a visual acuity chart on which optotypes per visual acuity value are provided for all visual acuity values may be placed in advance on the optical path L1, and the illumination light from the visible light source 11 to the optotypes 12a other than a desired visual acuity value is shielded by a filter to change over an irradiation position of the illumination light.

The visible light source 11 is configured to change an amount of light to be emitted in at least two levels; a first light amount and a second light amount lower (darker) than the first light amount. In the illumination light of the second light amount is emitted from the visible light source 11, the luminance of the background of the optotypes 12a to be presented to the eye E is decreased as compared with a case where the illumination light of the first light amount is emitted. On the other hand, even when the illumination light to be emitted from the visible light source 11 is changed from the first light amount to the second light amount, the luminance of the optotypes 12a is less changed than the luminance of the background. Accordingly, by emitting the illumination light of the second light amount from the visible light source 11, it is possible to reduce the contrast ratio between the optotypes 12a to be presented to the eye E and the background of the optotypes 12a than that in the case where the illumination light is emitted with the first light amount. Thus, even if the optotype plate 12 does not have the optotypes 12a different in color density, changeover of the light amount of the illumination light to be emitted from the visible light source 11 enables switching between a high contrast-ratio state where the contrast ratio of each optotype 12a for visual acuity test to be presented to the eye E and the background of each optotype 12a is high and a low contrast-ratio state here the contrast ratio is low. According to the optometric apparatus 1 of the present embodiment, therefore, the visual acuity measurement at high contrast and the visual acuity measurement at low contrast can be performed by use of the optotype plate 12 having no optotypes different in color density.

The contrast ratio between each visual acuity test optotype 12a to be presented to the eye E and the background thereof can be set in any range by adjustment of the amount of the light from the visible light source 11. The present embodiment is explained assuming that the contrast ratio between each optotype 12a and the background thereof under irradiation of the first light amount is 82% or more pursuant to the contrast ratio in a standard optometer. Further, the contrast ratio between each optotype 12a and the background thereof under irradiation of the second light amount is less than 25%. However, the present embodiment can be achieved by changing the amount of light to be emitted from the visible light source 11 between the first light amount and the second light amount to change the contrast ratio between each optotype 12a and the background thereof. For instance, the contrast ratio between each optotype 12a and the background under irradiation of the first light amount may be set to less than 82% without being pursuant to the contrast ratio in the standard optometer.

In the present embodiment, in the objective measurement of eye refractive power as well as in the high-contrast visual acuity measurement, the visible light source 11 is also turned on to emit light of the first light amount, the details of which will be mentioned later. Furthermore, even in the visual acuity measurement under glare lighting as well as the low-contrast visual acuity measurement, the visible light source 11 is turned on to emit light of the second light amount.

The visible light source 11 and the optotype plate 12 (the optotypes 12a) are moved together along the optical axis L1 by a drive mechanism 19 including a motor and a slide system. By movement of the visible light source 11 and the optotypes 12a, a fogging is applied to the eye E during the objective measurement. Further, by movement of the visible light source 11 and the optotypes 12a, a presenting position (a presenting distance) of the optotypes 12a with respect to the eye E is optically changed during the subjective measurement, thereby correcting an error of a spherical refractive power of the eye E. Specifically, moving the light projecting lens 13, the visible light source 11, and the optotype 12a constitutes an optical system for correcting spherical power. This spherical power correcting optical system is not limited to the above configuration and may be configured by moving the relay lens placed in the optical path in an optical axis direction.

The glare test optical system 40 in the present embodiment is an optical system including visible light sources (glare light sources) 41 and being configured to emit glare light to the eye E to which the optotypes 12a are presented from the optotype presenting optical system 10. The glare test optical system 40 includes for example two (a pair of) visible light sources 41 and a condenser lens 42. The two visible light sources 41 are turned off (unlighted) in the high-contrast visual acuity measurement, low-contrast visual acuity measurement, and objective measurement of eye refractive power, but are turned on (lighted) in the visual acuity measurement in a glare lighting state. Light beam emitted from the light sources 41 travel toward the eye E via the condenser lens 42 and the half mirror 16.

Figure 2:
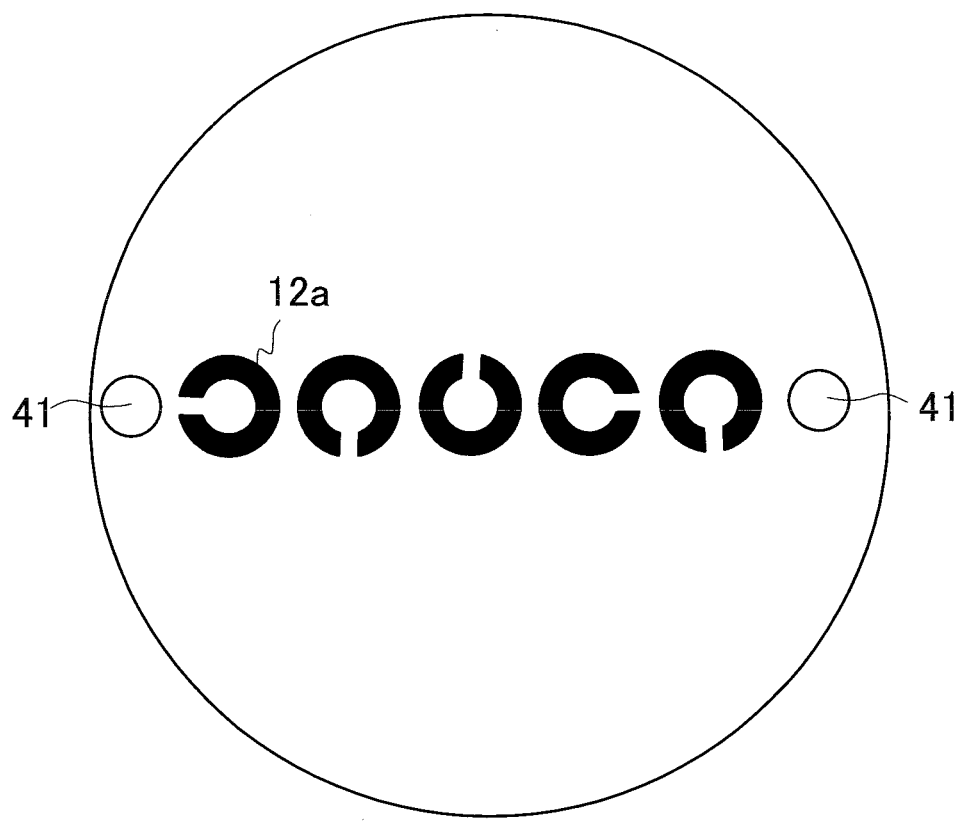
FIG. 2 is an explanatory view to explain an image to be presented to an examinee's eye in visual acuity measurement in a glare lighting state.

Herein, referring to FIG. 2, the visual acuity measurement in a glare lighting state will be explained. FIG. 2 is an explanatory view to explain an image to be presented to the eye E in the visual acuity measurement under glare lighting. In the present embodiment, as shown in FIG. 2, the two visible light sources 41 are arranged in such positions as to appear on right and left sides of the optotypes 12a. In the visual acuity measurement under glare lighting, the visible light sources 41 emit glare light around the outer circumference of the optotypes 12a. This glare light simulates headlights of a car. Accordingly, lighting of the glare light reproduces a situation that the examinee sees a car at night. For instance, if the examinee has a cataract, the glare light irradiated to the examinee's eye E is scattered by the opacity of a crystalline lens of the eye E, so that the optotype 12a is difficult to see. Therefore, based on an answer of the examinee, an examiner can estimate whether or not the eye E has a cataract.

Returning to FIG. 1, the explanation will be continued. The ring index projecting optical system 55 and the working distance index projecting optical system 56 are placed in front of an anterior segment of the eye E as shown in FIG. 1. The ring index projecting optical system 55 is an optical system for emitting near infrared light to project a ring index to a cornea Ec of the eye E. The ring index projected to the cornea Ec can be utilized as an index for measuring a corneal shape. The ring index projecting optical system 55 can also be used as an anterior segment illumination optical system for illuminating the anterior segment of the eye E. On the other hand, the working distance index projecting optical system 56 is an optical system for emitting near infrared light to project an infinite index to the cornea Ec of the eye E. Based on the position of the infinite index with respect to the cornea Ec, the position of the optometric apparatus 1 with respect to the eye E can be aligned.

A measurement optical system 70 includes a projecting optical system (a light projecting optical system) 70a and a light receiving optical system 70b. The projecting optical system (the light projecting optical system) 70a is an optical system for projecting a spot-shaped measurement index image to the fundus Ef of the eye E through a pupil center part of the eye E. The light receiving optical system 70b is an optical system for extracting reflection light from the fundus Ef as a ring shape through a pupil peripheral part to image a ring-shaped fundus reflection image.

The projecting optical system 70a shares the dichroic mirror 17 and the objective lens 18 with the optotype presenting optical system 10 and further includes a measurement light source 71, a relay lens 72, and a hole mirror 73, which are arranged on an optical axis L2 of the measurement optical system 70. The light source 71 is located in an optically conjugated position with a fundus Ef of an emmetropic eye. Further, an aperture of the hole mirror 73 is located in an optically conjugated position with a pupil of the eye E.

The light receiving optical system 70b shares the dichroic mirror 17 and the objective lens 18 with the optotype presenting optical system 10 and also the hole mirror 73 with the projecting optical system 70a. The light receiving optical system 70b further includes a relay lens 76 and a total reflection mirror 77 which are placed on the optical axis L2 corresponding to a reflecting direction of the hole mirror 73, a light-receiving diaphragm 78, a collimator lens 79, a ring lens 80, and a two-dimensional imaging device (a light-receiving device) 82 such as an area CCD which are placed on the optical axis L2 corresponding to a reflecting direction of the total reflection mirror 77. The light-receiving diaphragm 78 and the imaging device 82 are located in optically conjugated positions with the fundus Ef. The ring lens 80 consists of a ring-shaped lens part and a light shielding part applied with light-shielding coating in a region other than the lens part. This ring lens 80 is placed in an optically conjugated position with the pupil of the eye E. Output from the imaging device 82 is input to a calculation controller 100 (hereinafter, simply referred to as a controller 100).

The measurement optical system 70 is not limited to the above. Alternatively, any measurement optical system may be adopted as long as it includes a light projecting optical system for projecting measurement light toward a fundus Ef of an examinee's eye and a light receiving optical system including a light-receiving device for receiving reflection light obtained by reflection of the measurement light from the fundus Ef. For instance, the eye refractive power measurement optical system may also be configured to include a Shack-Hartmann sensor. Of course, another measurement type apparatus may be utilized (e.g., a phase difference type apparatus arranged to project slit light).

The observation optical system (the imaging optical system) 60 shares the objective lens 18 and the dichroic mirror 17 with the optotype presenting optical system 10 and further includes the half mirror 15, an imaging lens 61, and a two-dimensional imaging device 62. The two-dimensional imaging device 62 has an imaging plane placed in a substantially conjugated position with the anterior segment of the eye E. Output from the two-dimensional imaging device 62 is input to the controller 100 and thus an image of the anterior segment of the eye E imaged by the two-dimensional imaging device 62 is displayed on the monitor 7. This observation optical system 60 is also used as an optical system for detecting an alignment index image formed on the cornea Ec of the eye E. Based on an imaging result of the alignment index image by the two-dimensional imaging device 62, the position of the alignment index image is detected.

According to the present embodiment, as described above, it is possible to measure high-contrast visual acuity and low-contrast visual acuity by use of the index presenting optical system 10. Further, the objective measurement of eye refractive power can also be conducted by use of the index presenting optical system 10, the ring index projecting optical system 55, the working distance index projecting optical system 56, and the observation optical system 60, and the measurement optical system 70.

Meanwhile, on the optotype plate 12 of the index presenting optical system 10 in the present embodiment, a single fixation target for objective measurement of eye refractive power is arranged while a plurality of optotypes for visual acuity test are arranged for each visual acuity value. Thus, as the number of the visual acuity test optotypes is larger, an installation space of the index presenting optical system 10 is increased in the optometric apparatus 1. In addition, the index presenting optical system 10 in the present embodiment can share only the optical path from the eye E to the dichroic mirror 17 with the observation optical system 60 and the measurement optical system 70. This optical system 10 is independent from the ring index projecting optical systems 55 and the working distance index projecting optical systems 56. In a case where the number of optotypes for visual acuity test is increased in the optotype plate 12 of the index presenting optical system 10, leading to an increased installation space of the index presenting optical system 10, it is difficult for other optical systems 55, 56, 60, and 70 to absorb such an increased space. Specifically, when a conventional optometric apparatus having optical systems as in the present embodiment is to be used to measure both high-contrast visual acuity and low-contrast visual acuity, the whole optometric apparatus may be simply increased in size by the increased number of optotypes. In contrast, as described above, according to the optometric apparatus 1 of the present embodiment, the optotypes 12a used for high-contrast visual acuity measurement can also be used to measure low-contrast visual acuity. Accordingly, the optometric apparatus 1 can be prevented from increasing in size even though this apparatus can measure high-contrast visual acuity and low-contrast visual acuity and also objectively measure eye refractive power.

The control system of the optometric apparatus 1 will be explained below. The optometric apparatus 1 is provided with the controller 100 as a main control system. This controller 100 is a processing unit including an electronic circuit for performing control processing of each part or component and arithmetic processing of measurement results. The controller 100 is electrically connected to the visible light sources 11 and 41, the two-dimensional imaging devices 22 and 62, the motor 18, the drive mechanism 19, a memory 101, the monitor 7, and an operating part 90.

The memory 101 is a storage unit (not shown) including a program storage region for storing control programs for various controls of the optometric apparatus 1 to be executed by the controller 100 and a temporary storage region for temporarily storing measurement results such as visual acuity and eye refractive power. In the present embodiment, the memory 101 stores in advance a control program for a visual acuity measurement mode prepared to perform subjective visual acuity measurement in various conditions and a control program for an objective measurement mode to objectively measure eye refractive power. For the visual acuity measurement mode defined in this control program, there are prepared at least three types of modes; i.e., a normal mode for visual acuity measurement at high contrast, a low contrast mode for visual acuity measurement at low contrast, a glare mode for visual acuity measurement under glare lighting.

The operating part 90 is provided with a plurality of switches 90a, 90b, 90c, 90d, 90e, 90f, 90g, and 90h to input a signal corresponding to a selected operation under operation of an examinee to the controller 100. The switches 90a, 90b, 90c, and 90d are arranged to receive operations for switching the mode of the controller 100 to the objective measurement mode, the normal mode, the low contrast mode, and the glare mode, respectively.

The switches 90e and 90f are to be operated to change the visual acuity value of a presented optotype. In the visual acuity measurement mode, when an operation signal from the switch 90e or 90f is input to the controller 100, the controller 100 drives the optotype plate 12 to change a combination of the optotypes 12a to be placed on the optical axis L1. Accordingly, the optotypes 12a presented to the eye E are switched to another. To be concrete, when the switch 90e is operated, an optotype 12a is switched to another optotype 12a of a higher visual acuity value by one level than the current one. When the switch 90f is operated, the optotype 12a is switched to another optotype 12a corresponding to a lower visual acuity value by one level than the current one.

The switches 90g and 90h are to be operated to change the spherical power of a correcting lens. Under operations of the switches 90g and 90h, the controller 100 drives the light source 11 and the optotype plate 12 to move along the optical axis L1 to change the spherical power.

Measuring operations of the optometric apparatus 1 configured as above will be explained below.

<Visual Acuity Measurement Mode>

Figure 3:
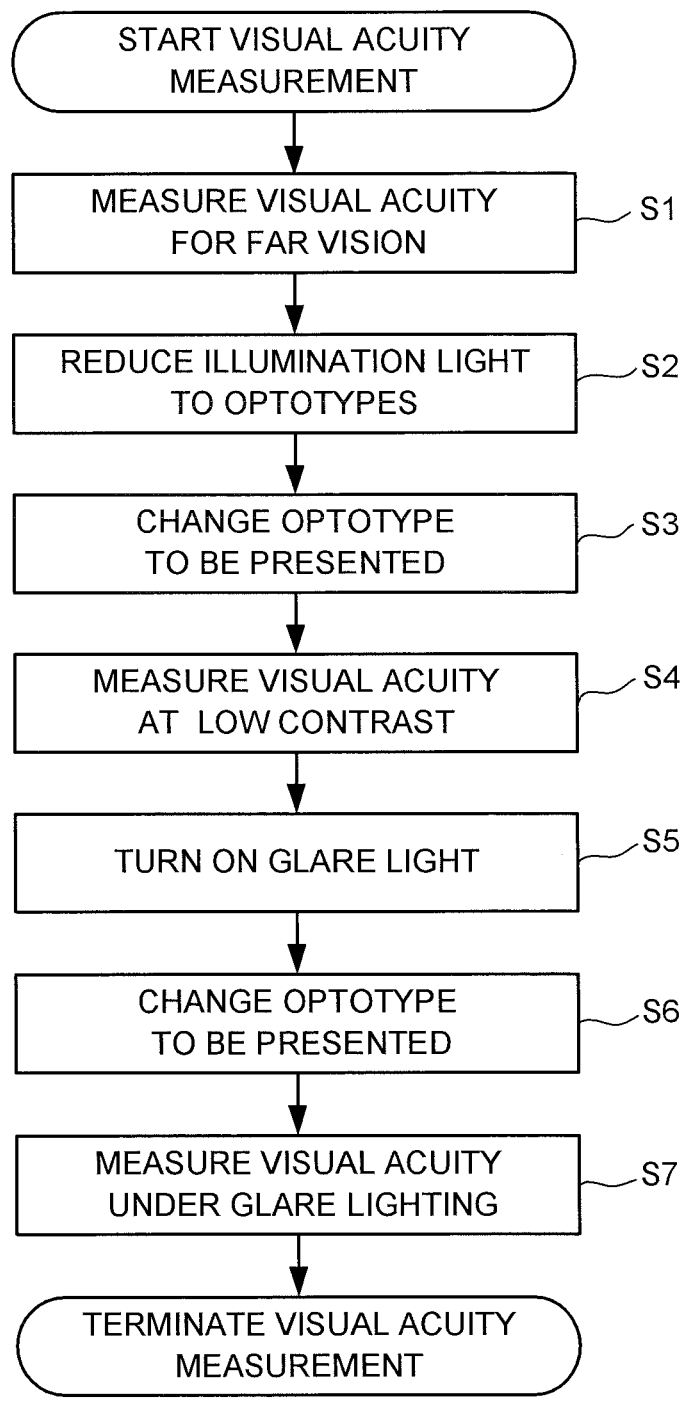
FIG. 3 is a flowchart showing one example of a flow of a test in a visual acuity measurement mode.

Referring to FIG. 3, a visual acuity measurement mode will be explained. FIG. 3 is a flowchart showing one example of a flow of the test in the visual acuity measurement mode. After startup of the optometric apparatus 1, when any of the switches 90b to 90d of the operating part 90 is operated, the controller 100 executes the control in the visual acuity measurement mode corresponding to the operated switch. In the optometric apparatus 1 of the present embodiment, each of the normal mode, the low contrast mode, and the glare mode can be switched from any mode. However, for convenience of explanation, the following explanation is given to a case where a test is conducted in each of the normal mode, the low contrast mode, and the glare mode in this order.

<Normal Mode>

After startup of the optometric apparatus 1, when the switch 90b is operated, the controller 100 executes control in the normal mode. This enables high-contrast visual acuity measurement, that is, visual acuity measurement which is normally performed (S1). In the normal mode, upon receipt of an operation signal from the switch 90b, the controller 100 turns on the visible light source 11 with the first light amount. The controller 100 drives the motor 18 to rotate the optotype plate 12 so that the optotypes 12a (a group of optotypes 12a) to be initially presented to the eye E are placed on the optical axis L1. At that time, in a case where the eye refractive power measured in the objective measurement mode has been stored in advance in the memory 101, the controller 100 causes a group of optotypes 12a of an estimated visual acuity value based on the stored refractive power to be placed on the optical axis L1. On the other hand, when the refractive power measured in the objective measurement mode has not been stored in advance in the memory 101, the controller 100 causes a group of optotypes 12a of a lowest visual acuity value (that is, a group of optotypes 12a of a visual acuity value of 0.1) to be placed on the optical axis L1 and presented to the eye E.

When the first optotypes 12a are presented to the eye E by the above operations, the examiner starts visual acuity measurement on the examinee. Based on an answer of the examinee, the examiner operates the switches 90e and 90f to switch the optotypes 12a to be presented to the eye E. For instance, when the examinee had a correct answer about the presented optotypes 12a, the examiner operates the switch 90e to switch the optotypes 12a to optotypes corresponding to a one-level higher visual acuity value. On the other hand, when the examinee had a wrong answer about the presented optotypes 12a, the examiner operates the switch 90f to switch the optotypes 12a to optotypes 12a corresponding to a one-level lower visual acuity value. By repeating the above steps, a maximum visual acuity value of the examinee, which is his/her recognizable limit, is examined.

When the maximum visual acuity value is obtained, the examiner operates the switches 90g and 90h to change the spherical power S in order to check the spherical power closest to a positive value at which the maximum visual acuity value is obtained. When the switch 90g or 90h is selected, the light source 11 and the optotype plate 12 are moved along the optical axis L1 to change the spherical power. Accordingly, the spherical power S closest to the positive value at which the maximum visual acuity value is obtained is determined and thus reference values in prescription for the powers of eyeglass lenses or contact lenses are obtained.

<Low Contrast Mode>

In the normal mode, when an operation signal of the switch 90c is input to the controller 100, the controller 100 executes control in the low contrast mode. In the low contrast mode, firstly, the controller 100 turns on the visible light source 11 to emit light with a light amount controlled to the second light amount reduced to be lower than the first light amount used in the normal mode (S2). Accordingly, the contrast ratio between each optotype 12a for visual acuity test to be presented to the eye E and the background of each optotype 12a is reduced to less than 25%.

Furthermore, at the time of changing the light amount from the visible light source 11 from the first light amount to the second light amount, the controller 100 drives the motor 18 to switch the optotypes 12a to be placed on the optical axis L1 (S3). At that time, on the optical axis L1, the optotypes 12a corresponding to a visual acuity value one level lower than the last optotypes 12a placed on the optical axis L1 in the normal mode is newly placed. For instance, in a case where the optotypes 12a corresponding to a visual acuity value of 0.5 are finally placed in the normal mode, optotypes 12a corresponding to a visual acuity value of 0.3, which is one level lower than the last one, is put on the optical axis L1. After the first optotypes 12a are presented to the eye E by the above operations, the examiner starts the visual acuity measurement at low contrast (S4). In the present embodiment, the low-contrast visual acuity measurement may also be conducted for example by examining the maximum visual acuity of an examinee, which is his/her recognizable limit, by changing the presenting optotypes different in visual acuity value in a similar manner to the high-contrast visual acuity measurement, while the second light amount is irradiated from the visible light source 11.

In the present embodiment, as above, at the time of changing the light amount from the visible light source 11 from the first light amount to the second light amount, the controller 100 switches the optotypes 12a to be presented to the eye E from the optotype presenting optical system 10. Accordingly, even when the high-contrast visual acuity measurement and the low-contrast visual acuity measurement are continuously performed, it is possible to measure the low-contrast visual acuity while avoiding the influence of the memory of the examinee who looked the last optotypes 12a presented in the high-contrast visual acuity measurement and the influence of his/her persistence of vision.

According to the present embodiment, furthermore, the optotypes 12a are switched by groups of optotypes 12a, provided one group for each visual acuity value, in the optotype plate 12. Accordingly, in an optometric apparatus having a plurality of optotype plates 12, for example, two types of visual acuity measurements can be continuously performed without switching the optotype plates 12 while avoiding the influence of examinee's memory of the last optotypes 12a and the influence of his/her persistence of vision. When the single optotype plate 12 is provided (when the optotypes 12a are provided in groups, one group for each visual acuity value) as in the present embodiment, two types of visual acuity measurements can be continuously performed while avoiding the influence of examinee's memory and the influence of his/her persistence of vision. Thus, the optotype presenting optical system 10 can be configured with a simple structure as in the present embodiment.

In the present embodiment, additionally, when the light amount from the visible light source 11 is changed from the first light amount to the second light amount, the optotypes 12a presented to the eye E are switched to optotypes 12a corresponding to a visual acuity value one level lower than the last optotypes 12a presented in the normal mode. Herein, it is generally known that the low-contrast visual acuity measurement performed using optotypes with a small contrast ratio to the background tends to bring a test result (a maximum visual acuity value) that is a lower visual acuity value than in the high-contrast visual acuity measurement using optotypes with a large contrast ratio to the background. Accordingly, since the optotypes 12a are switched to the optotypes 12a corresponding to a one-level lower visual acuity value when the light amount from the visible light source 11 is changed from the first light amount to the second light amount, the frequency of switching the optotypes 12a by the examiner is reduced. This can enhance measurement efficiency in the low-contrast visual acuity measurement performed continuously from the high-contrast visual acuity measurement.

<Glare Mode>

When an actuating signal from the switch 90d is input to the controller 100 in the low contrast mode, the controller 100 executes control in a glare mode. In this glare mode, the controller 100 first turns on the two visible light sources 41 of the glare optical system 40 (S5). Accordingly, glare light from the visible light sources 41 lights up in the form of spots near the outer periphery of the optotypes 12a presented to the eye E (see FIG. 2). A manner of lighting up the glare light is not limited thereto. Glare light may be emitted to surround the optotypes 12a.

When turning on the visible light sources 41 of the glare optical system 40, the controller 100 drives the motor 18 of the optotype presenting optical system 10 to selectively place the optotypes 12a on the optical axis L1 (S6). The optotypes 12a to be placed on the optical axis L1 at that time correspond to a lower visual acuity value by one level than the last optotypes 12a placed on the optical axis L1 in the low contrast mode.

When the first optotypes 12a are presented to the eye E by the above operations, the examiner starts visual acuity measurement on the examinee in a glare lighting state (S7). In the present embodiment, for example, the optotypes to be presented are switched under glare lighting in a similar manner to the visual acuity measurement in the normal mode and a maximum visual acuity of the examinee, which is his/her recognizable limit, is examined.

In the present embodiment, as described above, when the visible light sources 41 of the glare optical system 40 are to be turned on, the controller 100 switches the optotypes 12a to be presented to the eye E from the optotype presenting optical system 10. Even when the low-contrast visual acuity measurement and the visual acuity measurement in a glare lighting state are continuously performed, it is possible to measure the visual acuity in a glare lighting state while avoiding the influence of the memory of the examinee who looked the last optotypes 12a presented in the low-contrast visual acuity measurement and the influence of his/her persistence of vision.

According to the present embodiment, furthermore, the optotypes 12a are switched by groups of optotypes 12a per visual acuity value provided in the optotype plate 12. Therefore, in the optometric apparatus having a plurality of optotype plates 12, for example, two types of visual acuity measurements can be continuously performed without switching the optotypes 12a while avoiding the influence of examinee's memory and the influence of his/her persistence of vision. When the single optotype plate 12 is provided (when the optotypes 12a are provided in groups one for each visual acuity value) as in the present embodiment, two types of visual acuity measurements can be continuously performed while avoiding the influence of examinee's memory and the influence of his/her persistence of vision. Thus, the optotype presenting optical system 10 can be configured with a simple structure.

In the present embodiment, additionally, when the visible light sources 41 of the glare optical system 40 are to be turned on, the optotype 12a presented to the eye E are switched to optotypes 12a corresponding to a visual acuity value one level lower than the optotypes 12a presented before the visible light sources 41 are turned on. Herein, it is generally known that the visual acuity measurement performed while glare light is in a lighted state tends to result in a lower visual acuity value than in the visual acuity measurement while the glare light is in an unlighted state. Accordingly, since the optotypes 12a are switched to the optotypes 12a corresponding to a one-level lower visual acuity value when the visible light source 11 is turned on, the frequency of switching the optotypes 12a by the examiner is reduced. This can enhance measurement efficiency in visual acuity measurement under glare lighting continuously performed following the low-contrast visual acuity measurement.

Although the present embodiment uses the two glare light sources, a single glare light source may be used instead. As still another alternative, three or more glare light sources may be arranged to emit glare light so as to surround the optotypes 12a. Specifically, any configuration may be adopted as long as the influence of glare light can be judged.

In the present embodiment, the light sources 41 for glare test are provided in a different optical path from the optical path of the optotype presenting optical system 10. Alternatively, the light sources 41 for glare test may be provided in the common optical path with the optotype presenting optical system 10. For instance, the light sources 41 may also be provided outside the optotype plate 12 or outside the ring index projecting optical system 55 or working distance index projecting optical system 56. As still another alternative, the light sources 41 may be provided in front of the optotype plate 12. In short, any configuration may be adopted if only the glare light is made visible to an examinee.

The above explanation is given to the case where the low contrast mode is switched to the glare lighting mode, but the normal mode also may be switched to the glare lighting mode. In this case, the controller 100 brings the optotypes 12a corresponding to a lower visual acuity value by one level than the last optotypes 12a presented in the normal-mode visual acuity measurement onto the optical axis L1.

This case also can provide the same advantages as in the case of switching from the low contrast mode to the glare lighting mode.

As an alternative, when the normal mode, low contrast mode, or glare mode is to be switched to another mode, the visual acuity value of an optotype placed on the optical axis L1 of the optotype presenting optical system 10 may be stored as a test result obtained in a current mode in the memory 101. In addition, the visual acuity value stored in the memory 101 may be referred to when re-examination is performed in each mode. When the re-examination is performed in each mode, the optotypes 12a representing a previous test result may be placed on the optical axis L1. In this case, the re-examination can be started as a continuation of the previous examination. This can enhance examination efficiency.

The above explanation is given to the case where three types of visual acuity tests; the normal mode, the low contrast mode, and the glare mode, are continuously performed. An alternative is to perform any two of the modes, e.g., only the normal mode and the low contrast mode, in an arbitral order. Further, the visual acuity measurement may be conducted only in any one of the modes.

<Objective Measurement Mode>

When the optometric apparatus 1 is started up (for example, when the optometric apparatus 1 is powered on) or when the switch 90a is operated in any of the visual acuity measurement modes, the controller 100 performs control in an objective measurement mode. In this objective measurement mode, the controller 100 first controls driving of the motor 18 to set an optotype 12a (a fixation target) for objective measurement onto the optical path to apply a fogging to the eye E.

The examiner first instructs the examinee to fix his/her head on a face support unit not shown and fixate the fixation target, and then makes alignment of the optometric apparatus 1 with respect to the examinee's eye. Upon receipt of a measurement start signal, the controller 100 turns on the light source 71. Measurement light emitted from the light source 71 is projected onto the fundus Ef via the components from the relay lens 72 to the objective lens 18 to form a spot-shaped image of a point light source, the image being rotatable on the fundus Ef.

The light of the point-light-source image formed on the fundus Ef is reflected and scattered by the fundus Ef, and goes out of the eye E and is condensed by the objective lens 18. The light condensed by the objective lens 18 is condensed again on an aperture of the light-receiving diaphragm 78 via from the dichroic mirror 17 to the total reflection mirror 77, and is made into substantially parallel light (in the case of an emmetropic eye) by the collimator lens 79. This substantially parallel light is extracted as a ring-shaped light through the ring lens 80 and captured as a ring image by the imaging device 82.

At that time, the controller 100 first performs preliminary measurement of eye refractive power. Successively, the light source 71 and the relay lens 72 are moved along the optical axis L1 based on a result of the preliminary measurement, thereby applying a fogging to the eye E. Then, the eye E under fogging is subjected to the refractive power measurement.

An output signal from the imaging device 82 is stored as image data (measured image) in the memory 101 under the control of the controller 100. The controller 100 subsequently specifies (detects) the position of the ring image in each meridian direction based on the measured image stored in the memory 101. In this case, the controller 100 specifies the position of the ring image by edge detection. The position of the ring image may be specified based on a midpoint of a cut position in a waveform of a luminance signal cut by a predetermined threshold, a peak of the waveform of the luminance signal, a position of the center of gravity of the luminance signal, etc.

Successively, the controller 100 approximates the ring image to an elliptic shape by a least-square method or the like based on the specified position of the ring image. The controller 100 then obtains a refraction error in each meridian direction from the approximated elliptic shape, calculates the refractive power of the examinee's eye, i.e., S (Sphere power), C (Cylinder power), and A (Astigmatic axial angle), based on the refraction error, and then stores the measurement results in the memory 101 and displays them on the monitor 7.

As explained above, in the normal mode of the visual acuity measurement mode, when the measurement result obtained in the objective measurement mode is stored in advance in the memory 101, the optotypes 12a corresponding to a visual acuity value close to an estimated visual acuity value based on the measurement result are first presented to the eye E. In this case, accordingly, the visual acuity measurement can be started by presenting the optotypes 12a corresponding to a visual acuity value close to the visual acuity value of the eye E. Thus, the frequency of switching the optotypes 12a by the examiner is reduced. In the optometric apparatus 1 of the present embodiment, therefore, it is preferable to perform measurement of eye refractive power in the objective measurement mode and then switch to the normal mode to perform visual acuity measurement.

The present invention is not limited to the above embodiment and may be modified variously. For instance, the optometric apparatus 1 in the above embodiment is configured to switch the optotypes to be presented to the eye E to an optotype 12a corresponding to a lower visual acuity value by one level than a current one in each of the cases where the visual acuity measurement mode is switched from the normal mode to the low contrast mode (when the light amount to be emitted from the visible light source 11 of the optotype presenting optical system 10 is changed from the first light amount to the second light amount) and where the low contrast mode is switched to the glare mode (when the visible light sources 41 of the glare test optical system 40 are turned on). As an alternative, the optotypes 12a may be switched to an optotype 12a corresponding to a lower visual acuity value by two or more levels than a current one.

It may be arranged to decrease the visual acuity value of the optotypes 12a by different level(s) between the case of switching from the normal mode to the low contrast mode and the case of switching from the low contrast mode to the glare mode. For example, the presented optotypes 12a may be switched to an optotype 12a corresponding to a lower visual acuity value by one level when the normal mode is switched from the low contrast mode and the presented optotypes 12a may be switched to an optotype 12a corresponding to a lower visual acuity value by two levels when the low contrast mode is switched from the glare mode.

In each of the case of switching the visual acuity measurement mode from the normal mode to the low contrast mode and the case of switching from the low contrast mode to the glare mode, respectively, the optotypes 12a to be presented to the eye E may be switched to an optotype 12a corresponding to a higher visual acuity value than a current one. In such a case, similarly, the optotypes 12a to be presented to the eye E is switched to an optotype corresponding to a higher visual acuity when the visual acuity measurement mode is switched. This enables two types of visual acuity measurements to be continuously performed while avoiding the influence of examinee's memory and the influence of his/her persistence of vision.

The above embodiment shows the case where the optotypes 12a to be simultaneously presented to the eye E are provided in one group for each visual acuity value. As an alternative, the optotypes 12a to be simultaneously presented to the eye E may be provided in two or more groups for each visual acuity value. For instance, two or more groups of the optotypes 12a corresponding to the same visual acuity value are provided in the optotype plate 12. In this case, the optotypes 12a to be presented to the eye E can be switched to either one of an optotype corresponding to a lower visual acuity value, an optotype corresponding to a higher visual acuity value, and an optotype corresponding to the same visual acuity value, in each of the cases where the visual acuity measurement mode is switched from the normal mode to the low contrast mode and where the low contrast mode is switched to the glare mode. In any case, two types of visual acuity measurements can be continuously performed while avoiding the influence of examinee's memory and the influence of the of his/her persistence of vision. Furthermore, it may be arranged to provide two or more optotype plates provided with different optotypes per visual acuity value from plate to plate and change over one optotype plate to another to place an optotype(s) on the optical path L1 in each of the case of switching the visual acuity measurement mode from the normal mode to the low contrast mode and the case of switching the low contrast mode to the glare mode.

The above embodiment exemplifies that the optotype presenting optical system 10 includes the visible light source 11 configured to emit light with different light amounts selected based on operation of the switch 90c in order to change the amount of illumination light to be illuminated to the optotype plate 12. The optotype presenting optical system 10 is not limited to the above configuration. For instance, it may be arranged to provide two or more illumination light sources that emit light with different light amounts and to select the illumination light source to be turned on based on operation of the switch 90c. Furthermore, a filter may be placed between the light source and the optotype plate 12 to shield a part of illumination light from a light source based on operation of the switch 90c in order to change the light amount to be irradiated to the optotype plate 12.

In the above embodiment, the optometric apparatus 1 is explained as also having a configuration for measuring the objective refractive power. The configuration for measuring the objective refractive power (e.g., the ring index projecting optical system 55, the working distance index projecting optical system 56, the observation optical system 60, and the measurement optical system 70) do not always have to be provided to implement the present invention. The present invention is also applicable to an optometric apparatus other than the optometric apparatus configured to perform the objective refractive power measurement, for example, applicable to an automatic optometer.

In the above embodiment, the optometric apparatus 1 is explained as being configured to measure the visual acuity under glare lighting using the glare optical system 40. The glare optical system 40 does not always have to be provided to implement the present invention. Such a configuration also can switch the optotypes 12a to be presented to the eye E to an optotype corresponding to a lower visual acuity value by one level when the visual acuity measurement mode is switched from the normal mode to the low contrast mode. As a result, two types of visual acuity measurements can be continuously performed while avoiding the influence of examinee's memory and the influence of his/her persistence of vision. Accordingly, the frequency of switching the optotypes 12a by the examiner to measure the low-contrast visual acuity can be reduced.

In the above embodiment, while the visual acuity measurement mode is being executed as the glare mode, the controller 100 causes the visible light source 11 to irradiate the illumination light of the second light amount to perform the visual acuity measurement. As an alternative, while the visual acuity measurement mode is executed as the glare mode, the controller 100 may cause the visible light source 11 to irradiate the illumination light of the first light amount to perform the visual acuity measurement.

Reference Signs List
10 Optotype presenting optical system
11 Visible light source
12a Optotype
18 Motor
40 Glare test optical system
100 Controller

What is claimed is:

1. An optometric apparatus comprising:
   an optotype presenting part, including a plurality of optotypes corresponding to visual acuity to be measured, the optotype presenting part is configured to present part of the plurality of optotypes to an examinee's eye; and
   a controller configured to perform simultaneously:
   (i) switching a measurement mode of a visual acuity test between a first measurement mode and a second measurement mode wherein the second measurement mode is either a low contrast mode in which an optotype is presented at lower contrast than in the first measurement mode or a glare mode for visual acuity measurement to be performed in a glare lighting state, and
   (ii) switching the optotypes to be presented to the examinee's eye by the optotype presenting part from a first one or more optotypes of the plurality of optotypes presented during the first measurement mode to a second one or more optotypes of the plurality of optotypes which are presented during the second measurement mode and wherein at the time of the switching from the first measurement mode to the second measurement mode, the controller switches to the second one or more optotypes of the plurality of optotypes that correspond to a lower visual acuity value from the first one or more optotypes of the plurality of optotypes presented during the first measurement mode.

2. The optometric apparatus according to claim 1, further comprises an illumination light source to irradiate illumination light to at least part of the plurality of optotypes,
   wherein at the time of switching from the first measurement mode to the second measurement mode, the controller changes output of the illumination light source or drives a filter for restricting light traveling from the illumination light source toward the plurality of optotypes to change a light amount of the illumination light to be irradiated to the plurality of optotypes from a first light amount to a second light amount lower than the first light amount.

3. The optometric apparatus according to claim 1, further comprises a glare light source to emit glare light to the examinee's eye,
   wherein at the time of switching from the first measurement mode to the second measurement mode, the controller switches the glare light source from an unlighted state to a lighted state.

4. The optometric apparatus according to claim 1, further comprises:
   a light projecting optical system configured to project measurement light toward a fundus of the examinee's eye; and
   a light receiving optical system including a light-receiving device to receive reflection light of the measurement light reflected by the fundus of the examinee's eye,
   wherein the controller is configured to obtain an objective value of eye refractive power of the examinee's eye based on a light reception result of the light-receiving device.

5. The optometric apparatus according to claim 4,
   wherein the optotype presenting part is placed on an optical axis independent from the light projecting optical system and the light receiving optical system.

6. The optometric apparatus according to claim 1,
   wherein the controller is configured to cause the optotype presenting part to first present an optotype corresponding to a visual acuity value according to an objective value of the eye refractive power in the first measurement mode.

7. An optometric apparatus comprising:
   an optotype plate having a plurality of optotypes corresponding to visual acuity to be measured;
   an optotype presenting part configured to selectively present part of the plurality of optotypes of the optotype plate to an examinee's eye;
   an illumination light source to irradiate illumination light to the optotype plate; and
   a controller configured to perform simultaneously:
   (i) changing output of the illumination light source or drive a filter for restricting light traveling from the illumination light source toward the optotype plate to change a light amount of the illumination light to be irradiated to the optotype plate from a first light amount to a second light amount lower than the first light amount, and
   (ii) switching the plurality of optotypes to be presented to the examinee's eye by the optotype presenting part from a first part of the plurality of optotypes of the optotype plate to a second part of the plurality of optotypes of the optotype plate;
   wherein the controller performs (i)-(ii) simultaneously such that the first light amount is changed to the second light amount at the same time as when the first part of the plurality of optotype of the optotype plate is changed to the second part of the plurality of optotypes of the optotype plate, and wherein the second part of the plurality of optotypes corresponds to a lower visual acuity value than the first part of the plurality of optotypes.

8. An optometric apparatus comprising:
   an optotype plate including a plurality of optotypes corresponding to visual acuity to be measured;
   an optotype presenting part configured to selectively present part of the plurality of optotypes of the optotype plate to an examinee's eye;
   a glare light source configured to emit glare light to the examinee's eye; and a controller configured to:
- (i) switch the glare light source from an unlighted state to a lighted state, and
- (ii) simultaneous with switching the glare light source, switch from a first part of the plurality of optotypes to be presented to the examinee's eye by the optotype presenting part to a second part of the plurality of optotypes of the optotype plate, such that the first part of the plurality of optotypes is presented to the examinee's eye during the unlighted state and the second part of the plurality of optotypes is presented to the examinee's eye during the lighted state, wherein the second part of the plurality of optotypes corresponds to a lower visual acuity value than the first part of the plurality of optotypes.

9. The optometric apparatus according to claim 1, wherein a first optotype of the second one or more optotypes of the plurality of optotypes presented after the switching from the first measurement mode to the second measurement mode further corresponds to a lower visual acuity value by one level than a prior optotype presented in the first measurement mode.

\* \* \* \* \*